United States Patent [19]
Brennan

[11] Patent Number: 5,514,179
[45] Date of Patent: May 7, 1996

[54] MODULAR FACIAL IMPLANT SYSTEM

[76] Inventor: H. George Brennan, 501 Evening Star La., Newport Beach, Calif. 92660

[21] Appl. No.: 105,408

[22] Filed: Aug. 10, 1993

[51] Int. Cl.⁶ .................................. A61F 2/28; A61F 2/02
[52] U.S. Cl. ............................................... 623/16; 623/11
[58] Field of Search ................................. 623/10, 11, 16, 623/20, 23

[56] References Cited

U.S. PATENT DOCUMENTS

| | | | |
|---|---|---|---|
| 4,790,849 | 12/1988 | Terino | 623/11 |
| 4,955,917 | 9/1990 | Karpf | 623/22 |
| 5,047,058 | 9/1991 | Roberts et al. | 623/11 |
| 5,195,951 | 3/1993 | Giampapa | 623/16 |
| 5,314,480 | 5/1994 | Elloy et al. | 623/16 |

FOREIGN PATENT DOCUMENTS 2447182  9/1980  France ....................... 623/11

OTHER PUBLICATIONS

Archives of Otolaryngology Val 108 pp. 441–444 (1982) H. C. Brennan.

Primary Examiner—Debra S. Brittingham
Attorney, Agent, or Firm—Michael G. Petit

[57] ABSTRACT

A modular prosthesis for implantation beneath the skin is described. The modular prosthesis comprises a universal shell, which is relatively thin and substantially planar, having the general size and shape required for the prosthesis. The prosthesis is a composite structure consisting of the universal shell and one or more shims. The shims are individually cut from a shim sheet of a biocompatible material of suitable thickness. The shim sheet has a shell-contacting surface with means thereon for attaching the shim to the shell. The shims are cut from the shim sheet and attached to the shell to construct a prosthesis providing the desired contour to the overlying tissue following implantation. In a preferred embodiment, the universal shell and the shims have releasable interlocking means therebetween which permits changing the shims or adding shims to the prosthesis as required.

1 Claim, 2 Drawing Sheets

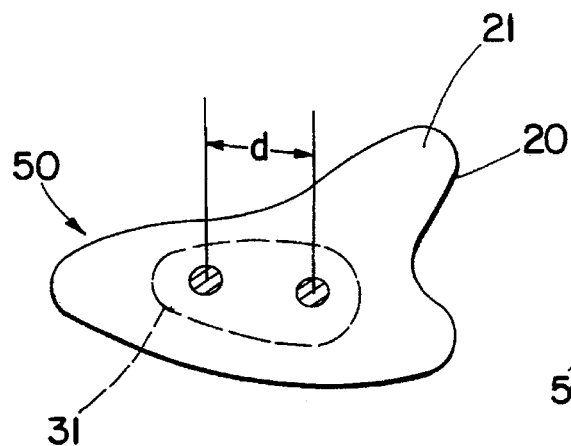
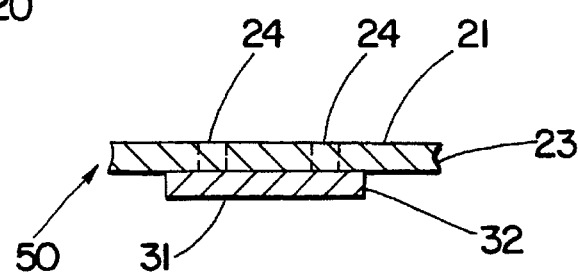
Fig. 5(a)  Fig. 5(b)
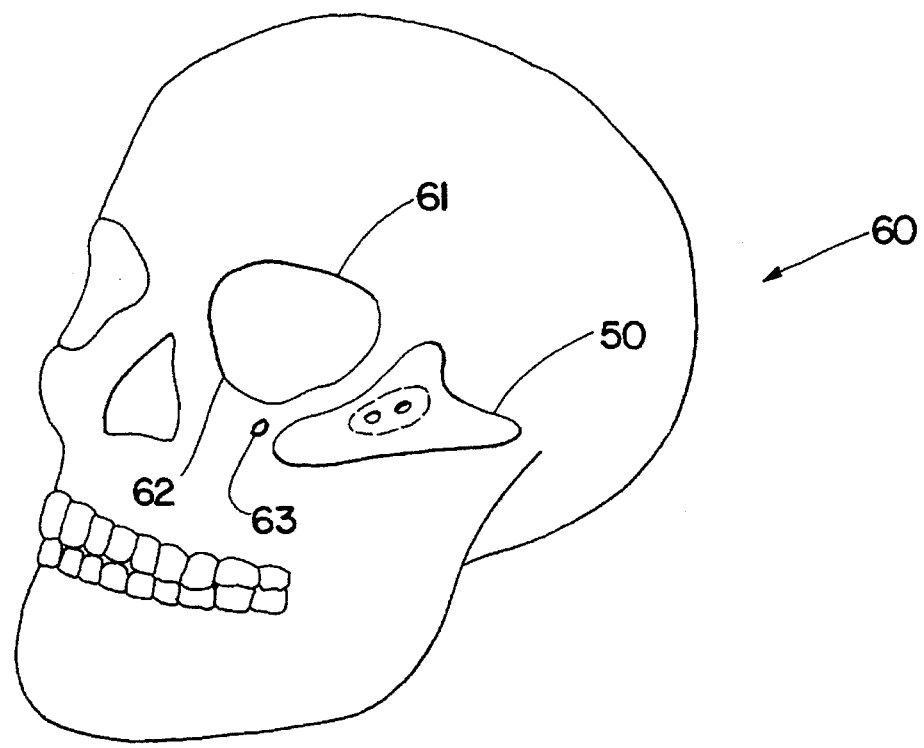
Fig. 6

MODULAR FACIAL IMPLANT SYSTEM

BACKGROUND OF THE INVENTION

1. Field of the Invention

The present invention provides a surgical prosthesis for facial augmentation and more particularly a modular implantable prosthesis having a variable thickness and contour.

2. Description of Prior Art

The skeletal framework of the face determines many of the relationships between features of the face which will produce either an attractive or unattractive appearance. Prominences or weaknesses in features are related to the underlying bony structure in the face. It is possible to augment weaknesses of the skeletal framework using facial implants to enhance or create prominences. In addition, although not pertinent to the instant invention, it is possible to sculpt the appearance of the face by reducing the projection of underlying bone in areas that are not ideal. Facial implants offer a means of improving the foundation of an unattractive face. By the use of such implants it is possible to convert concavities to convexities, create more of an oval-shaped face by enhancing the prominence of certain areas of the face, and generally improve the overall aesthetic appearance.

The most commonly used facial implant is the chin implant. The second most commonly used facial implant is the malar or cheek implant. The sub-malar and mid-facial implant are also frequently used, and, less frequently, implants augmenting the temple and forehead are employed. Among the newest are supraorbital and mandibular augmentation implants. Many other implants and techniques of skeletal augmentation are known and commonly used by the plastic surgeon. A summary of such procedures is set forth, for example, in AESTHETIC FACIAL SURGERY (Raven Press, 1991) authored by the present inventor.

Malar implants are well known in the art. An example is provided by the present inventor in the ARCHIVES OF OTOLARYNGOLOGY, Vol. 108, pp 441–444, (July, 1982) and in U.S. Pat. No. 4,790,849 issued Dec. 13, 1988 to Terino. The foregoing references generally describe an anatomical implant suitable for positioning between the malar zygomatic bone complex and the fleshy portion of the side of the face commonly referred to as the cheek for increasing the prominence of the cheek below the eye orbit of the patient. Such an implant will raise the cheeks giving the underlying cheekbones a more prominent appearance and imparting a more handsome and pleasing appearance to the facial features of the patient. Such implants are commercially available and are sold in a variety of sizes for a particular shape. In accordance with current practice, once a shape is selected, the surgeon must search through the inventory of existing sizes to find the best fit for a particular patient. In some instances more than one implant may be required to augment different portions of the facial skeleton during a procedure. Such a selection is usually a compromise and does not provide an exact fit. It is, therefore, desirable to provide a single modular implant having the flexibility to be adapted to fit and anatomically conform to the underlying bone structure of any particular patient to provide a desired elevation of the overlying tissue.

SUMMARY OF THE INVENTION

An object of the present invention is to provide an implantable modular prosthesis which, in combination, can be assembled from component parts to produce a composite prosthesis adapted to a particular patient.

It is yet another object of this invention to provide a modular facial implant which consists of a shell, or primary outermost surface, generally anatomically adapted to the host site, and one or more shims adapted to attach to the shell to build up portions thereof to enhance the projection of the overlying tissue and to conform to .the contour of the underlying skeletal structure of the face.

It is yet another object of this invention to provide a modular implantable prosthesis whereby the prosthesis may be assembled from component parts to more particularly take on the desired contour of the face prior to implantation.

Another object of the invention is to provide a modular implantable prosthesis which may be modified following implantation to adjust the projection of the overlying tissue in relation to the underlying skeletal structure.

These and other objects of the invention will become apparent as we turn now to the preferred embodiments.

BRIEF DESCRIPTION OF THE DRAWINGS

FIG. 5 is a perspective view (a) and end-on view (b) of the shim and implant composite with the connecting tabs cut off to conform to the outer surface of the individual shell.

FIG. 6 is a perspective view of an embodiment of the modular facial implant properly positioned below the patients orbit with it's position slightly below the orbital notch avoiding the infraorbital foramen.

DETAILED DESCRIPTION OF THE PREFERRED EMBODIMENTS

Figure 1:
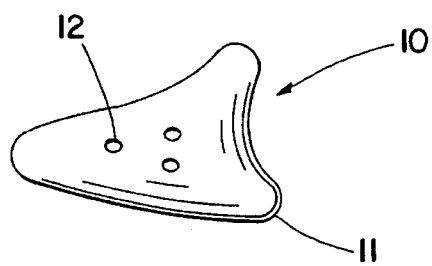
FIG. 1 is a perspective view of a malar implant according to the prior art.

While the present invention is best taught by means of an example drawn from the prior art, the invention is understood to not be limited to any particular implant or to any particular embodiment selected for exemplary purposes from the prior art. Turning now to FIG. 1, an embodiment of a malar implant according to the prior art is illustrated. The implant 10, while it may be of uniform thickness, generally has a 3-dimensional asymmetric configuration. There is an outer or skin-facing surface 11, illustrated as a generally convex surface having a area of greatest prominence at the apex at the lower mid region of the outer surface 11. The outer surface 11 forms a prominent cheekbone when the implant 10 is implanted in the patient. Fenestrations 12 extending from the outer surface 11 to the inner surface provide channels for tissue ingrowth which stabilizes the implant.

The inner surface is a generally concave surface or deep recess in the back side of the implant which forms a complementary fit with the skeletal tissue underlying the cheek of the patient. Such an implant is generally referred to as an anatomical implant. The cheekbone region includes the maxillary zygomatic bones which form the maxillary zygomatic complex. The cheekbone is the prominence below the eye formed by the zygomatic prong. The malar bone is a four-pointed bone on each side of the face uniting the frontal and superior maxillary bones with the zygomatic process of the maxilla.

It is known in the art that different patients require different shapes and sizes of protheses for building up or augmenting the malar zygomatic complex and/or the submalar area. Thus, the surgeon must have access to an inventory of different sizes and shapes of implants. Prior to surgery, the surgeon must measure the patient to determine which implant is the correct size and shape. Then the correct implant; that is, the implant providing the "best fit" is retrieved from the inventory and, if not already sterile, it is sterilized prior to implantation. As stated earlier, it is common that none of the sizes in the inventory is the exact fit for the particular patient. In such cases, the off-the-shelf implant coming the closest to the ideal is selected.

Figure 2:
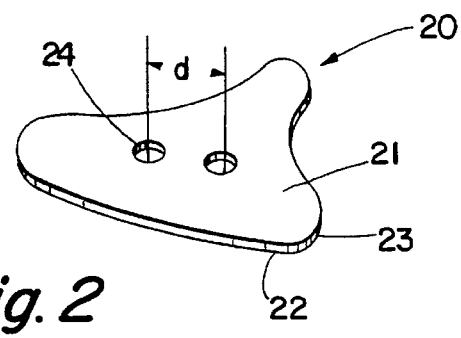
FIG. 2 is a perspective view of the universal shell portion of a modular malar implant in accordance with a preferred embodiment of the present invention.
Figure 3:
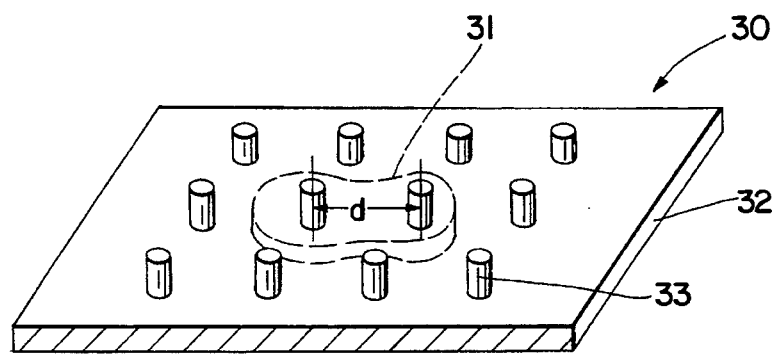
FIG. 3 is a perspective view of a generalized shim sheet which may be cut to form a shim as shown in phantom.

FIG. 2 shows a universal shell 20 which is a modular component of the implant of the present invention and which may be cut from a sheet of biocompatible elastomer to have a shape approximating the overall shape of, for example, the prior art implant 10. The universal shell 20, which has an upper skin-facing surface 21 and a shim-contacting surface 22, is thinner than the implant 10 because it is meant to be used together with a modular shimming system to build up the shell over the underlying skeletal tissue to approximate the desired overall contour. Thus, the shell 20 may be cut with a pair of scissors or other tool to the correct shape as is required for the particular procedure, and patient. The shim 31 (FIG. 3) may then be cut and positioned against the shim-contacting surface 22 of the universal shell 20 to build a prosthesis having desired projection in specific areas. The shell 20 and shim 31 together form the modular implant of the present invention. In order for the combination or composite modular implant to form a more or less integral structure, means for attaching the shim 31 to the shell 20 are necessary. One such means comprises holes or fenestrations 24 cut in the universal shell 20 to matingly receive protuberances 33 on the shell-contacting surface of a shim 31. In the preferred embodiment, the shim sheet, generally indicated at 30, from which individual shims 31 may be cut, comprises a substantially planar sheet of a biocompatible polymer with protuberances 33 thereon. The protuberances 33 are spaced a distance d apart. The protuberances 33 may have an expansion-type locking means thereon such as a barbed tip 41 or a mushroom tip 42 to securely hold the shim 31 to the shell 20. Holes or fenestrations 24 are then cut in the universal shell 20 such that they can matingly receive the protuberances 33. An actual shim 31, shown in phantom in FIG. 3, may be cut from the shim sheet 30. Shim sheets can be provided in a variety of thicknesses.

In practice, the surgeon may have the patient come in prior to surgery for a fitting. The fitting consists of applying the universal shell 20 to the patient's cheek, cutting it to size and cutting shims 31 to make the overall outer curvature and projection aesthetically pleasing prior to implantation. The shims 31 are cut from the shim sheet 30 and placed on the universal shell. In a preferred embodiment, tissue ingrowth fenestration (not shown) are punched through the prosthesis at the time of surgery. Alternatively, the tissue ingrowth fenestrations are incorporated into the (molded) shell and shim sheets in such a way that when the modular implant is assembled, the tissue ingrowth fenestrations in the shell and shim(s) are in alignment. A mirror image of the prosthesis is made for the other side of the face. Then, sometime prior to surgery, the composite modular implants (prostheses) are sterilized and readied for implantation. Alternatively, sterile shim sheets and shells can be used to assemble a modular implant at the time of surgery.

Figure 4A:
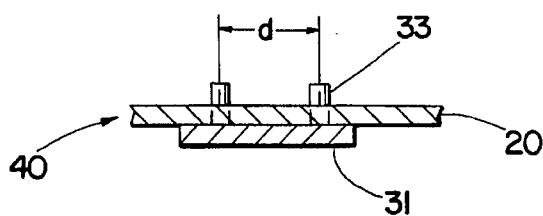
FIG. 4(a) is a side view of the universal shell of FIG. 2 and the shim of FIG. 3 brought together so as to form a composite implant.
Figure 4B:
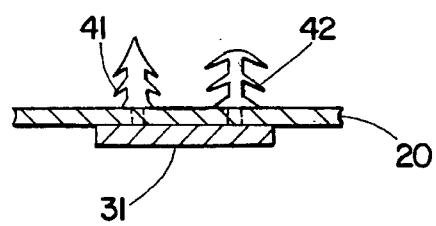
FIG. 4(b) is the same as FIG. 4(a), but shows examples of various expansion types of locking means on the end of the attachment protuberances.

The manner in which the composite implant comprising the universal shell 20 module and the shim 31 module are assembled into a more or less integral modular implant is shown more clearly in FIGS. 4 and 5. FIG. 4(a) is an end view of a shim 31 having a thickness 32 bearing protuberances 33 on its upper or shell-contacting surface pressed onto the bottom or shim-contacting surface 22 of a universal shell 20 having a thickness 23. The protuberances 33 project above the upper tissue-facing surface 21 of the universal shell 20. As previously stated, the protuberances 33 may have means thereon such as a barb 41 or a mushroom cap 42 to lockingly engage the shell 20. FIG. 5(a) shows the relative positions of the composite shims 31 and the universal shell 20 in the modular prosthesis 50. The shim 31 and shell 20 in the modular prosthesis 50 may be glued together with a medical grade RTV compound such as Silastic® or they may simply be pressed together and held in place by friction. It is most preferable to punch the attachment holes 24 in the universal shell 20 with a coring punch. This removes the material from the universal shell 20 to matingly receive the protuberances 33 in the shim 31. The punch is preferably a multiple-hole punch where the center of the two holes to be punched are separated by a distance d. After the holes 24 are punched in the universal shell 20 and the shim 31 is positioned correctly against the shell 20, then ingrowth fenestrations may be punched in the implant to penetrate both the shim and shell thereby providing space for tissue ingrowth to promote fixation and stabilization of the implant following implantation. These ingrowth fenestrations (not shown) may conveniently be molded into the shim sheet 30 coaxial with and central to the protuberances 33. Such ingrowth fenestrations in the prosthesis are preferably located near the center of the implant so that if it becomes necessary at a later date to remove the implant for further shimming or reduction, the tissue holding the implant in place can be easily snipped. Wherever the fenestrations are located, it is particularly desirable that the tissue ingrowth fenestrations extend from the skin-facing surface of the shell portion through to the tissue-facing surface of the shin portion of the implant.

It is important that the modular prosthesis does not delaminate or otherwise disintegrate following implantation. For example, tissue ingrowth between the shim 31 and the universal shell 20 may force them apart. Thus, the interface between the shim 31 and the universal shell 20 should be designed to discourage organized tissue ingrowth therebetween. One possible way of achieving this may be by making the upper shell-contacting surface of the shim 31 and the bottom shim-contacting surface 22 of the shim 31, which surfaces contact each other in the implant 50, open cell or otherwise disorganized but pervious to tissue ingrowth. Alternately, a silastic adhesive or viscous silicone gel may be used to exclusively fill the interface between the shim and the shell.

While a particular embodiment of the present invention has been illustrated and described, it would be obvious to those skilled in the art that various other changes and modifications can be made without departing from the scope of the invention. For example, the modular nature of the prosthetic implant described herein can be applied to any implantable prosthesis requiring a custom fit to the underlying supportive structure and a particularly desirable projection of the overlying tissue. Chin, temple and forehead implants, for example, as well as any implant adapted to augment an anatomical site may be custom fabricated using the shim and shell type of modular system described herein. In addition to the protuberances discussed above, the means for connecting the shims to the shell may vary. For example, mating "hook-and-loop" type of connectors may be molded into contacting surfaces of the shim sheet and the shell sheet respectively. Or the shim and shell may be joined with adhesive. Or a combination of such means of connection may be employed. It is, therefore, intended to cover in the appended claims all such changes and modifications that are within the scope of the invention.

What I claim is:

1. A modular implant for use in cosmetic and reconstructive surgery for placement beneath the skin and supportive underlying tissue of a patient comprising, in combination, a shim portion and a shell portion, said shell portion being an elastomeric member having a shim-contacting surface having at least two holes therein and a skin-facing surface and wherein said shim portion consists of a substantially planar elastomeric member having a shell-contacting surface and a tissue-facing surface and wherein said shell-contacting surface of said shim has at least two protuberances projecting therefrom operable for lockingly engaging said at least two holes on said shim contacting-surface of said shell and wherein following implantation within the body of a patient said implant is operable for changing the contour and/or elevation of the skin with respect to the supporting underlying tissue.

* * * * *